Figures 1, 2:
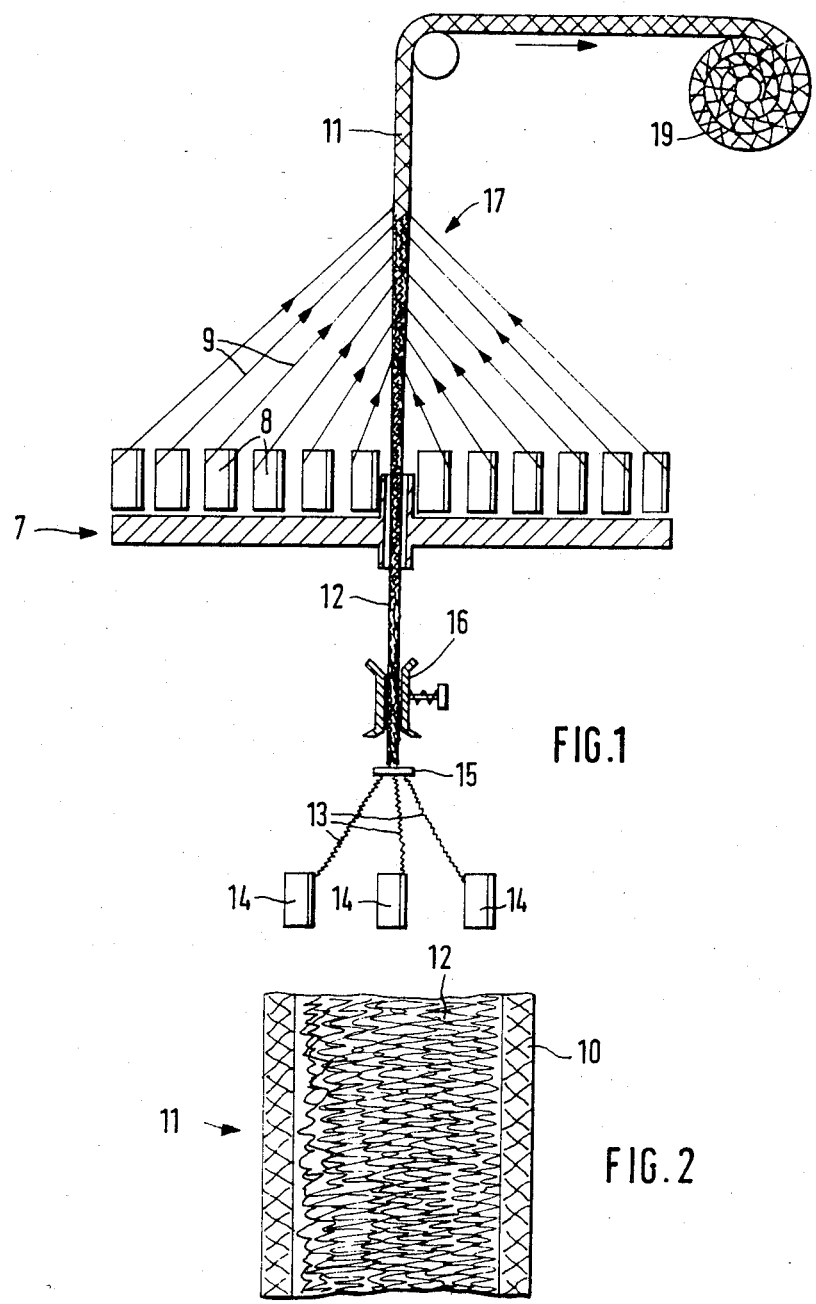

United States Patent [19]

Planck et al.

[11] Patent Number: 4,546,769
[45] Date of Patent: Oct. 15, 1985

[54] SUTURE THREAD

[75] Inventors: Heinrich Planck, Nurtingen; Wolfgang Joas, Reutlingen, both of Fed. Rep. of Germany

[73] Assignee: Institute fur Textilund Faserforschung, Stuttgart, Fed. Rep. of Germany

[21] Appl. No.: 579,964

[22] Filed: Feb. 14, 1984

Related U.S. Application Data

[63] Continuation of Ser. No. 291,052, Aug. 7, 1981, abandoned.

[30] Foreign Application Priority Data

Aug. 16, 1980 [DE] Fed. Rep. of Germany ....... 3030972

[51] Int. Cl.$^4$ ............................................. A61L 17/00
[52] U.S. Cl. ....................... 128/335.5; 87/6
[58] Field of Search ..................... 128/335.5; 87/6, 8; 428/37, 222

[56] References Cited

U.S. PATENT DOCUMENTS 2,841,046  7/1958  Runton ................................ 87/6 X
3,187,752  6/1965  Glick ................................ 128/335.5
3,565,077  2/1971  Glick ................................ 128/335.5

Primary Examiner—Michael H. Thaler
Attorney, Agent, or Firm—Antonelli, Terry & Wands

[57] ABSTRACT

A suture thread which comprises a jacket (or sheath) of a tubular braided structure made of yarns which are not crimped and a core located within the jacket containing crimped fibers. The jacket is formed by braiding the non-crimped yarns around the core.

27 Claims, 2 Drawing Figures

U.S. Patent

Oct. 15, 1985

4,546,769

SUTURE THREAD

This is a continuation of application Ser. No. 291,052, filed Aug. 7, 1981, now abandoned.

The invention relates to a suture thread having a tubular jacket made of non-crimped yarns and a core within the jacket made of crimped yarns, and to a process for producing the thread.

In the conventional suture threads, the jacket and the core consist of yarns which are not crimped, wherein, if the core has several yarns, these yarns are twisted to form a ply yarn; these yarns also consist of materials which can be degraded in the human body (e.g., polyglycolic acid) or which cannot thus be degraded (for example polyester, polyamide, polypropylene). In particular, the jacket and the core can be made of synthetic fiber yarns, preferably of filaments, the materials of which have thus been produced by chemical methods. These involve especially filaments of synthetic resin or viscose, but other synthetic fiber substances are likewise suitable. It is also possible to make the yarns of natural fibers, or with a natural fiber content, preferably natural silk. The term "filament" is understood to mean a synthetically produced, monofil fiber as formed by means of a die orifice of a spinneret or multiple-orifice spinneret. Such filaments are also called endless fibers, elemental threads, capillaries, monofilaments. A yarn consisting of a plurality of such filaments is called "multifilament yarn."

"Braid number" is understood to mean the number of braids present per French inch (=27.07 mm) in the jacket along a surface line (also called spine) axially parallel to the longitudinal axis of the thread.

The following symbols are furthermore employed:

$Z$ = number of braids according to the above definition, i.e., based on a French inch $K$ = braider bobbin number (the number of braider bobbins corresponds to the number of braider bobbins of the braiding machine utilized during braiding of the tubular braided work forming the jacket, i.e., the number of bobbins with braiding yarns utilized for the braiding step)

$N$ = number of yarns of the core; in case of a ply yarn, the yarns forming same are counted individually $GT$ = individual fiber weight of the single yarn, expressed in terms of yarn weight in grams per 10 kilometers, i.e., decitex (dtex)

$f$ = number of filaments of the individual multifilament yarn

USP Size = classification of suture threads into varying diameter ranges, published in *United States Pharmacopoeia* XIX, pp. 468,665, Pharma Copiae Convention Inc. Meeting at Washington, D.C., April 1970, 12601 Twinbrook, U.S.A.

Heretofore the core of such suture threads consisted of a single multifilament yarn or a single ply yarn of twisted together multifilament yarns, wherein the filaments and thus also the multifilament yarns and ply yarns were not crimped. As a result, the core substantially determined the knot tear strength of the thread. Legal minimum values for the knot tear strength are specified for suture threads. These prescribed minimum knot tear strength values result in relatively high bending resistances of the suture threads in the heretofore conventional cores of ply yarns which are not crimped. This relatively high bending resistance, however, has certain disadvantages; in particular, this value has a disadvantageous effect on "handling" i.e., the manipulation of the thread during suturing. Also, the relatively high bending resistance has an unfavorable effect on the knot bond, i.e., the firmness with which the knot is tied.

Therefore, it is an object of the invention to provide a suture thread of the type described in the foregoing which has reduced bending resistance, i.e., $\frac{1}{2}$ to $\frac{1}{4}$ of the bending resistance of known suture threads so that its handling is easier during suturing, the thread is more supple, in particular, and also results in an improved knot tightness of the knots produced therewith.

This object has been attained according to the invention by providing that the core disposed within the jacket has crimped fibers.

The suture thread of this invention, thanks to the crimped fibers of its core, exhibits a lower bending resistance than the previous suture threads with cores of ply yarns without crimping. This facilitates the handling of the thread during operations and also improves the seat of the knot. Also, the thread of the invention is clearly more supple than the previously known suture threads of comparable diameters and fiber materials.

Preferably all fibers of the core can be crimped. However, it is also possible to incorporate into the core likewise some fibers without crimping, if the axial elasticity of the suture thread is to be reduced.

In the thread according to the present invention, it is no longer the core which, as was the case previously, determines essentially the knot tear strength; rather, the knot tear strength of the suture thread of this invention is more than heretofore influenced by the braided jacket, at least within specific elongation limits. The more elastic the core in the axial direction, the more the jacket is governing the knot tear strength, and, preferably, the provision can be made that the core has such a high axial elasticity that the jacket substantially determines the knot tear strength. The knot tear strength is the same or higher than the knots tear strength of known suture threads, because the jacket is made by more filaments as known, so it is more polymer-material in the jacket.

Therefore, a further advantage of the suture thread of this invention resides in that it can be made axially more elastic and extensible (elongatable) than the conventional suture threads, based on threads having the same USP size. The higher axial elasticity of the suture thread of this invention also results in an especially firm seat of the knot.

In spite of the higher axial elasticity of the thread of this invention, it also provides a good knot-shifting characteristic, thanks to its lower bending resistance, i.e., a knot formed in the thread can be displaced relatively easily along the thread to more the knot more closely to the sutured wound. The knot shifting ability can even be frequently better than in the conventional threads.

The jacket of the thread according to the invention can be fashioned in a conventional way. In general, it is even more advantageous if, as compared with the heretofore customary jackets of the same USP size, the braider bobbin number K of the jacket is enlarged and the braid number Z is reduced. Thereby the handling of the thread can in some cases be even further improved and the knot shift even further facilitated. Preferably, the braider bobbin numbers K and braid numbers Z are as follows: with a suture thread of USP size 5-0, a braider bobbin number K of 10 or 12 and a braid number Z of 10-20; with a suture thread of USP size 4-0 or 3-0, a braider bobbin number K of 10, 12, or 14 and a braid number Z of 15-25; with a suture thread of USP size 2-0, a K of 12, 14 or 16 and a Z of 17-27; with a suture thread of USP size 0 or 1, a K of 14, 16, 18, 20 or 24 and a Z of 14-27; with a suture thread of USP size 2 or 2 and 4, a K of 16, 18, 20, 22, 24 or 26 and a Z of 17-30; with a suture thread of USP size 5, a K of 18, 20, 22, 24 or 26 and a Z of 17-30; and with a suture thread of USP size 6, a K of 20, 22, 24 or 26 and a Z of 17-30. Also, due to such braider bobbin numbers and braid numbers, which are especially advantageous according to the invention, the surface of the jacket becomes smoother, especially if this jacket, as preferably provided, is braided from multifilament synthetic yarns or natural silk yarns.

Although it has been known to improve the surface smoothness of suture threads by a subsequently applied, smooth coating, consisting of a so-called film-forming agent and adhering to the jacket, this step considerably raises the expenses in manufacturing the thread and further increases the bending resistance of the thread.

The core of the thread of this invention can consist especially advantageously of several doubled multifilament yarns. The term "doubled multifilament yarns" means that these "core yarns" during braiding enter the braiding point in parallel to the longitudinal axis of the thread being produced, i.e., they are not twisted together into a ply yarn. These yarns retain this axially mutually parallel, untwisted arrangement even after being encompassed by the jacket which is braided therearound.

If all doubled "core yarns" are crimped, as is preferably provided in accordance with this invention, the elasticity of this core is especially high. In case of threads of a small diameter, it can frequently be sufficient to make the core from a single multifilament yarn, preferably in case of threads of USP size 5-0. With threads of USP size 4-0 and larger, however, the core can suitably consist of a plurality of multifilament yarns.

The construction of the core from doubled multifilament yarns has also the advantage that the roundness of the thread is better than with the use of ply yarn as the core. Yet, the invention can also be applied in conjunction with a core made from one or more crimped ply yarns, namely, if the axial elasticity of the thread is to be lower than is the case with a core constructed from double, crimped multifilament yarns. For the same purpose, the core can frequently also consist of a tubular (hose-like) braided structure. Such a core furthermore affords increased resistance against nonuniform cross-sectional deformation by mechanical transverse (shear) pressures. If the core has a tubular braided structure, the provision can also be made in case of thicker threads that additionally one or several multifilament yarns or monofilaments are inserted in this "core braid structure" which yarns or monofilaments may not be crimped, either, in some cases.

Even if the core does not contain a braided core tube, the provision can be made in some instances that the core contains, besides the crimped filaments, also at least one filament which is not crimped, extending, for example, in parallel to the longitudinal axis of the core and is employed to somewhat reduce the axial elasticity of the thread. The bending resistance of even such a suture thread, likewise falling within the scope of this invention, is still significantly lower than that of comparable, conventional suture threads, the core of which consists all the way through of filaments which are not crimped.

The elastic extensibility of the suture thread of this invention can be still further raised by pretensioning its core axially. Thereby, the core contracts the jacket somewhat axially, the yarns of the jacket not being crimped, so that the jacket and thus the thread can then be subjected to stronger axial elastic elongations. To produce such a suture thread with an axially prestressed core, a process is provided according to this invention which is characterized in that the crimped filaments, yarns, or ply yarns constituting its core are pretensioned on their way to the braiding site and are braided around in the pretensioned condition by the braiding yarns supplied by the braider bobbins to the braiding site.

However, it is also possible to produce suture threads according to this invention without a pretensioned core, by allowing the fibers or fiber composites constituting the core to run to the braiding site without pretensioning or with only insubstantial pretensioning. Thereby, more voluminous, softer suture threads are obtained than with the use of a prestressed core, but these threads have a lower axial elastic extensibility than comparable threads with pretensioned axial core.

The drawing illustrates embodiments of the invention, to wit:

FIG. 1 shows a schematic view of a braiding machine for the production of a suture thread fashioned according to this invention; and FIG. 2 shows a partial longitudinal section through a suture thread according to one embodiment of the invention in a greatly enlarged representation.

The braiding machine 7, according to FIG. 1, exhibits in this embodiment twelve braider bobbins 8, i.e., yarn spools on which the non-crimped braiding yarns 9, are disposed, which are braided into the jacket 10 (FIG. 2), of a suture thread 11, to be manufactured on this braiding machine. The core 12, of this thread to be braided consists of several crimped, doubled yarns 13, preferably of multifilament yarns, which are taken off bobbins 14, and run together to a yarn guide 15, and from there through a yarn brake 16, adjustable in its pretensioning to the braiding point 17, where they are surrounded by braiding with the braiding yarns 9, i.e., the jacket 10, encompassing the core 12, is braided from the braiding yarns 9. The manufacture of this suture thread takes place continuously, and the thread is wound up to a coil 19.

The short fragmentary view of a thread 11, according to this invention, illustrated in a longitudinal sectional view in FIG. 2, shows its essentially cylindrical jacket 10, consisting of a tubular braided structure, a core 12, being located in the interior of the jacket, this core consisting of a plurality of crimped multifilament yarns extending axially within the jacket.

The peripheral surface of this suture thread can preferably be constituted by the braiding yarns of the jacket in its entirety. However, it is also possible to additionally provide this jacket with a finish improving, for example, its slip property or imparting to the jacket other desirable properties. For example, the jacket can be provided with a preparation or with a spotwise applied coating composition to alter its surface properties in a desirable fashion.

Instead of making the core 12, from at least one multifilament yarn, which is preferably done, it is also possible in some cases to make the core from monofilaments which are not twisted together or from at least one crimped ply yarn or, as mentioned above, the core can also consist of a tubular braided structure or can contain such monofilaments or fiber composites.

In the conventional suture threads, the individual multifilament yarns of the jacket and of the core have a so-called protective twist, i.e., a minor turn (for example 10-130 rotations/meter, depending on the individual fiber weight). This can also suitably be the case with the suture thread of this invention if its core and/or jacket exhibit multifilament yarns. However, it is frequently also suitable to provide turn-free (no-twist) multifilaments yarns for the core and/or for the jacket.

The following table lists constructions of several especially preferred embodiments for the suture threads of this invention.

The filaments of these suture threads in these embodiments can consist, for example, of polyester, but also of other basic fiber-forming materials of substantially the same specific weight. The crimping of the fibers of the core can be produced on different ways, for example by textronomy such as by false twisting or the same. Good results are obtained with a so called "Hochbanschfam", a false twist yarn with high elasticity, which has a crimpcontraction of about 60-65% for example, measured according to DIN 53840.

TABLE

| USP Size | Jacket Braided from Multifilament Yarns Which Are Not Crimped | | | | Core Made of Multifilament Yarns Which Doubled and Crimped | | |
|---|---|---|---|---|---|---|---|
| | K | GT (dtex) | f | Z | N | GT (dtex) | f |
| 5-0 | 12 | 25 | 22 | 18 | 1 | 50 | 24 |
| 4-0 | 12 | 25 | 22 | 20 | 3 | 50 | 24 |
| 3-0 | 12 | 49 | 16 | 18 | 3 | 50 | 24 |
| 2-0 | 16 | 49 | 16 | 23 | 6 | 50 | 24 |
| 0 | 16 or 24 | 49 | 16 | 25 | 8 | 50 | 24 |
| 1 | 18 or 24 | 49 | 16 | 21 or 27 | 10 or 12 | 50 | 24 |
| 2 | 24 | 49 | 16 | 27 | 12 | 50 | 24 |
| 3 and 4 | 20 | 113 | 32 | 25 | 20 | 50 | 24 |
| 5 | 20 | 113 | 32 | 21 | 30 | 50 | 24 |
| 6 | 24 | 113 | 32 | 19 | 35 | 50 | 24 |
| 2 | 18 | 113 | 32 | 21 | 12 | 50 | 24 |
| 3 and 4 | 24 | 95 | 24 | 19 | 20 | 50 | 24 |
| 5 | 24 | 95 | 24 | 19 | 25 | 50 | 24 |

What is claimed is:

1. A suture thread which comprises a jacket of a tubular braided structure made of yarns which are not crimped, said jacket having been produced by braiding around a core made of fibers, and said core located within the jacket containing crimped fibers; said jacket having a tubular braided structure braided from a number of multi-filament braid yarns taken from braider bobbins, the number of multifilament yarns used during the braiding of the jacket being greater as compared with conventional suture threads of the same diameter range (USP size) and the number of braids per unit length being smaller as compared with said conventional suture threads.

2. A suture thread according to claim 1, wherein all fibers forming the core are crimped.

3. A suture thread according to claim 1, wherein the core consists of fibers in the form of doubled yarns.

4. A suture thread according to claim 1, wherein the core has a tubular braided structure.

5. A suture thread according to claim 1, wherein the core consists of a ply yarn of crimped fibers.

6. A suture thread of USP size 5-0 according to claim 1, wherein said jacket is braided with a braider bobbin number K of 10 or 12 and a braid number Z of 10-20, and wherein K is the number of braider bobbins used during braiding of said jacket and Z is the number of braids per French inch.

7. A suture thread of USP size 4-0 or 3-0 according to claim 1, wherein said jacket is braided with K being 10, 12 or 14 and Z being 15-25, and wherein K is the number of braider bobbins used during braiding of said jacket and Z is the number of braids per French inch.

8. A suture thread of USP size 2-0 according to claim 1, wherein said jacket is braided with K being 12, 14 or 16 and Z being 17-27, and wherein K is the number of braider bobbins used during braiding of said jacket and Z is the number of braids per French inch.

9. A suture thread of USP size 0 or 1 according to claim 1, wherein said jacket is braided with K being 14, 16, 18, 20 or 24 and Z being 14-27, and wherein K is the number of braider bobbins used during braiding of said jacket and Z is the number of braids per French inch.

10. A suture thread of USP size 2 or 2 and 4 according to claim 1, wherein said jacket is braided with K being 16, 18, 20, 22, 24 or 26 and Z being 17-30, and wherein K is the number of braider bobbins used during braiding of said jacket and Z is the number of braids per French inch.

11. A suture thread of USP size 5 according to claim 1, wherein said jacket is braided with K being 18, 20, 22, 24 or 26 and Z being 17-30, and wherein K is the number of braider bobbins used during braiding of said jacket and Z is the number of braids per French inch.

12. A suture thread of USP size 6 according to claim 1, wherein said jacket is braided with K being 20, 22, 24 or 26 and Z being 17-30, and wherein K is the number of braider bobbins used during braiding of said jacket and Z is the number of braids per French inch.

13. A suture thread according to claim 1, wherein said core has an axial elasticity value so that the knot tear strength of the thread is essentially determined by the jacket.

14. A suture thread according to claim 1, wherein said core is axially pretensioned.

15. A process for the production of a suture thread according to claim 14, wherein said crimped fibers constituting the core are pretensioned on their way to the braiding site and, in the pretensioned condition, are surrounded by braiding with the braiding yarns supplied by the braider bobbins to the braiding site.

16. A suture thread according to claim 1, wherein said jacket is braided from multifilament yarns which are not crimped and which have a minor twist or are devoid of any twist.

17. A suture thread according to claim 1, wherein said jacket has a tubular braid structure braided from a number of multi-filament braid yarns taken from braider bobbins, the number of braider bobbins used during the braiding of the jacket being greater as compared with conventional suture threads of the same diameter range (USP size) and the number of braids per unit length being smaller as compared with said conventional suture threads.

18. A suture thread according to claim 1, wherein said core located within the jacket contains crimped fibers comprising a false twist yarn having high elasticity having a crimped contraction of about 60-65%.

19. A suture thread according to claim 1, wherein said suture thread has a reduced bending resistance on the order of $\frac{1}{2}$ to $\frac{1}{4}$ that of the bending resistance of a suture thread having a core consisting of non-crimped fibers.

20. A suture thread according to claim 1, wherein the fibers in the core are synthetic fibers.

21. A suture thread according to claim 20, wherein the synthetic fibers are filaments.

22. A suture thread according to claim 1, wherein the fibers forming the core are natural silk-fibroin fibers or fibers of polyglycolic acid.

23. A suture thread according to claim 1, wherein said suture thread has a reduced bending resistance on the order of ½ to ¼ of that of the bending resistance of a suture thread having a core consisting of non-crimped fibers.

24. A suture thread according to claim 23, wherein all fibers forming the core are crimped.

25. A suture thread according to claim 23, wherein said core located within the jacket contains crimped fibers comprising a false twist yarn having high elasticity exhibiting a crimped contraction of about 60–65%.

26. A suture thread according to claim 23, wherein said core is axially pretensioned.

27. A process for the production of a suture thread according to claim 26, wherein said crimped fibers constituting the core are pretensioned on their way to the braiding site and, in the pretensioned condition, are surrounded by braiding with the braiding yarns supplied by the braider bobbins to the braiding site.

* * * * *